United States Patent [19]

Kanaoka et al.

[11] 4,332,717

[45] Jun. 1, 1982

[54] PURIFICATION OF HUMAN GROWTH HORMONE

[75] Inventors: Masaharu Kanaoka, Takarazuka; Hideki Yanagi, Toyonaka; Shigeo Ogino, Nishinomiya, all of Japan

[73] Assignee: Sumitomo Chemical Company, Ltd., Osaka, Japan

[21] Appl. No.: 180,178

[22] Filed: Aug. 21, 1980

[30] Foreign Application Priority Data

Aug. 21, 1979 [JP] Japan .................. 54/106808

[51] Int. Cl.³ .................. A61K 35/55; C07G 7/00
[52] U.S. Cl. .................. 260/112 R; 424/108
[58] Field of Search .................. 260/112 R; 424/108

[56] References Cited

U.S. PATENT DOCUMENTS

| | | | |
|---|---|---|---|
| 3,409,605 | 11/1968 | Florini | 260/112 R |
| 4,000,098 | 12/1976 | Hofstee | 260/112 R |
| 4,006,059 | 2/1977 | Butler | 260/112 R |
| 4,115,375 | 9/1978 | Pedersen | 260/112 R |

OTHER PUBLICATIONS

Biochimica et Biophysica Acta, 74, pp. 525-531 (1963), Roos et al.
Acta Endocrinologica, 66, pp. 478-490 (1959), Trygstad et al.
J. Endocrinology, 23, pp. 285-290 (1961), Wallace et al.
Endocrinology, 77, pp. 559-563, Reisfeld et al. (1965).
Chem. Abst., 78, 1973, 133023s, Hofstee.
Int. J. Protein Res. I, pp. 85-92 (1969), Fönss-Bech et al.
Chem. Abst. vol. 83, 1975, 189954s, Hofstee.
Analytical Biochemistry 52, 430-448 (1973), Hofstee.
Biochemical and Biophysical Research Communications, vol. 50, No. 3, pp. 751-757, Hofstee, 1973.
Biochemical and Biophysical Research Communications, vol. 63, No. 3, pp. 618-624, Hofstee, 1975.
J. Macromol. Sci.-Chem. A 10 (122), pp. 111-147 (1976), Hofstee.
J. of Chrom. 11 (1978), 193, pp. 153-163, Hofstee et al.

*Primary Examiner*—Howard E. Schain
*Attorney, Agent, or Firm*—Sughrue, Mion, Zinn, Macpeak and Seas

[57] ABSTRACT

A method for purifying human growth hormone which comprises purifying an aqueous solution of crude human growth hormone by chromatography using a water-insoluble carrier having hydrophobic groups. High purity human growth hormone can be obtained by this hydrophobic interaction chromatography.

9 Claims, No Drawings

PURIFICATION OF HUMAN GROWTH HORMONE

BACKGROUND OF THE INVENTION

1. Field of the Invention

The present invention relates to a method for isolation and/or purification of human growth hormone by a hydrophobic interaction chromatography.

2. Description of the Prior Art

Purification procedures of human growth hormone are disclosed in many publications, for example:
(1) Biochimica et Biophysica Acta, 74, 525(1963),
(2) Federation Proceedings, 16, 775(1957),
(3) Endocrinology, 77, 1126(1965),
(4) Recent Progress in Hormone Research, 15, 71(1959), and
(5) Acta Endocrinologica, 66, 478(1971).

For the purpose of clinical use, the purification of human growth hormone should be carried out under mild conditions so that the denaturation of human growth hormone is minimized. In addition, since human pituitary glands are so limited in amount, an efficient procedure for isolation of human growth hormone must be employed from the view point of saving the limited natural resources.

A typical process for extracting and purifying human growth hormone which has heretofore been employed comprises:
(1) extracting frozen pituitary glands with a neutral or weakly basic buffer,
(2) subjecting the extract to precipitation with a precipitant,
(3) extracting the resulting precipitate with a neutral or weakly acidic buffer, and
(4) purifying the extract by column chromatography (e.g. gel filtration using Sephadex ®G etc., ion-exchange chromatography using DEAE-cellulose etc.).

However, the other pituitary hormones cannot be removed satisfactorily and, in addition, some salts contaminate the human growth hormone by these known processes.

DETAILED DESCRIPTION OF THE INVENTION

In order to eliminate such drawbacks of the conventional methods, we have made an intensive study, and have found that the crude human growth hormone which contains certain unsuitable salts and some other pituitary hormones can be effectively purified by a chromatography using a water-insoluble carrier having hydrophobic groups and that highly purified human growth hormone containing no or a very small amount of impurities can be obtained by the process of the present invention.

Accordingly, the present invention provides an improved method for purifying crude human growth hormone which is characterized by purifying a crude human growth hormone by a chromatography using a water-insoluble carrier having hydrophobic groups.

The human growth hormone to be purified in the present invention is an aqueous solution of crude human growth hormone partially purified by a conventional method. This starting material can be obtained, for example, by extracting human pituitary glands, cultured cells or cultured fluids, including fermentation products by recombinant DNA technique, by a conventional method (e.g. methods disclosed in the above publications).

In carrying out the present invention, a column is packed with a water-insoluble carrier having hydrophobic groups whose weight is 30 to 100 times that of the crude human growth hormone. And the column is washed with 1 to 3 bed volume each of distilled water, alcohol (e.g. methanol, ethanol), and distilled water, successively, followed by equilibrated with an aqueous solution of inorganic salt.

An aqueous solution of crude human growth hormone is placed on the column, and chromatography is carried out by eluting with only an aqueous solution of inorganic salt or an aqueous solution of inorganic salt and then distilled water. For example, impurities are eluted first with an aqueous inorganic salt solution (total molar concentration; $\leq 0.5$ M), and thereafter human growth hormone of high purity is eluted with an aqueous inorganic salt solution of total concentration lower than that of the solution above or distilled water.

When an aqueous solution of sodium hydrogenphosphate and/or sodium chloride are used, impurities are eluted first with the aqueous solution of inorganic salt of a concentration of 0.01 M, and highly purified human growth hormone is eluted with distilled water. Other useful substance which the crude human growth hormone may contain is also separated therefrom by eluting with the aqueous solution having an adequate concentration within a range from 0.01 M to 0.5 M.

The concentration of inorganic salts employed in the initial stage of elution is preferably equal to or less than that of inorganic salts in the crude human growth hormone solution.

For pre-equilibration of the carrier, the same aqueous solution as above is used in the present invention.

The inorganic salt used in the method of the present invention may be sodium hydrogenphosphate, sodium chloride, ammonium sulfate, potassium hydrogenphosphate, and a mixture thereof, among which sodium hydrogenphosphate and sodium chloride are preferred. The pH of the aqueous inorganic salt solution can be pH 4 to 9, and preferably pH 6 to 8. The most adequate flow rate of the eluant should be variable according to the volume of the column, the concentration and pH of the eluant and the sorts of eluants.

The water-insoluble carrier having hydrophobic groups of the present invention includes crosslinked agarose gels imparted with hydrophobic groups, such as alkyl groups, e.g., octyl group, etc., phenyl group and the like, examples of which are commercially available Phenyl-Sepharose ® CL-4B (Pharmacia), Octyl-Sepharose ® CL-4B (Pharmacia) etc., and porous resin composed of crosslinked polystyrol and having network structure, for example, Amberlite ® XAD's (Organo) etc.

The method of the present invention will be more particularly illustrated by the following examples, but the present invention is not limited thereto.

EXAMPLE 1

Twenty six ml of sodium phosphate buffer (0.025 M, pH 6.2) was added to frozen human pituitary glands (1.7 g) and the mixture was homogenized. The homogenate was centrifuged and the supernatant fluid was adjusted to pH 7.2 with 0.2 N sodium hydroxide. To the extract equal volume of saturated ammonium sulfate was added followed by stirred for 1 hour at 0° C. and left overnight at 0° C. The mixture was centrifuged and the precipitate was extracted with 1.8 ml buffer(A). Buffer(A) is composed of 0.3 M sodium chloride and 0.1 M sodium phosphate (pH 6.6). The extract of the precipitate (100 μl) was applied on a column of Phenyl-Sepharose ® CL-4B (bed volume, 10 ml) and the column was eluted with buffer(A) 10 ml, buffer(B) 30 ml, twice-diluted solution of buffer(B) 30 ml, and 10 times diluted solution of buffer(B) 30 ml successively. Buffer (B) is composed of 0.1 M sodium phosphate (pH 6.6). Then the column was eluted with distilled water and the fraction corresponding to elution volume 9 to 18 ml was collected. The collected fraction gave only one band corresponding to human growth hormone in a SDS-polyacrylamide gel electrophoresis.

EXAMPLE 2

The extract of precipitate of Example 1 (1.5 ml) was applied on a column charged with Sephadex ® G-100 (25 mmφ×900 mm) and the column was eluted with buffer(A). The fraction corresponding to elution volume 300 to 342 ml was collected.

On a column charged with 10 ml of Phenyl-Sepharose ® CL-4B, 4 ml of the collected fraction was applied. The column was eluted with successive buffer(A) 10 ml, 10 times-diluted solution of buffer(B) 30 ml, and distilled water. The fraction corresponding to elution volume 49 to 58 ml was collected.

The collected fraction gave two bands corresponding to intact human growth hormone and desamide form in a polyacrylamide gel electrophoresis, and only one band corresponding to human growth hormone in a SDS-polyacrylamide gel electrophoresis.

The contents of the other pituitary hormones in the human growth hormone purified by Phenyl-Sepharose ® column chromatography were compared with those in the human growth hormone purified by Sephadex ® G-100 gel filtration. The contents of PRL, LH, FSH and ACTH in the former were 1/100, 1/3, 1/5 and 1/20 respectively compared to those in the latter. Thus it is clear that highly purified human growth hormone can be obtained by the hydrophobic interaction chromatography.

What we claim is:

1. A method for purifying human growth hormone comprising the steps of:

contacting an aqueous solution of crude human growth hormone with a compound selected from the group consisting of crosslinked agarose having hydrophobic groups or porous resin composed of crosslinked polystyrol and having network structure; and separating and recovering a purified human growth hormone.

2. A method according to claim 1 wherein an aqueous inorganic salt solution, distilled water or a mixture thereof is employed as an eluant.

3. A method according to claim 1, wherein the hydrophobic groups are alkyl groups or phenyl groups.

4. A method as claimed in claim 2, wherein impurities are eluted first with an aqueous inorganic salt solution, and thereafter human growth hormone of high purity is eluted with an aqueous inorganic salt solution of lower concentration or distilled water.

5. A method as claimed in claim 4, wherein said aqueous inorganic salt solution for elimination of impurities has a concentration of 0.01 M to 0.05 M, and the elutant for recovering human growth hormone is distilled water.

6. A method according to any of claims 2, 3 or 4, wherein the inorganic salt is one or more selected from sodium hydrogenphosphate, sodium chloride, ammonium sulfate and potassium hydrogenphosphate.

7. A method according to claim 6, wherein the inorganic salt is sodium hydrogenphosphate, sodium chloride or a mixture thereof.

8. A method according to any of claims 2, 6 or 7, wherein the pH of the aqueous inorganic salt solution is 4 to 9.

9. A method according to claim 8, wherein the pH of the aqueous inorganic salt solution is 6 to 8.

* * * * *